(12) United States Patent
Endo et al.

(10) Patent No.: US 7,855,165 B2
(45) Date of Patent: Dec. 21, 2010

(54) HERBICIDE COMPOSITION FOR PADDY FIELD

(75) Inventors: Keiji Endo, Ibaraki (JP); Shinichi Shirakura, Tochigi (JP); Shin Nakamura, Tochigi (JP); Natsuko Minegishi, Tochigi (JP)

(73) Assignee: Bayer Cropscience AG (DE)

( * ) Notice: Subject to any disclaimer, the term of this patent is extended or adjusted under 35 U.S.C. 154(b) by 1014 days.

(21) Appl. No.: 11/622,514

(22) Filed: Jan. 12, 2007

(65) Prior Publication Data

US 2007/0167328 A1  Jul. 19, 2007

(51) Int. Cl.
*A01N 43/64* (2006.01)
*A01N 43/60* (2006.01)

(52) U.S. Cl. .................... 504/134; 504/136
(58) Field of Classification Search .......... None
See application file for complete search history.

(56) References Cited

FOREIGN PATENT DOCUMENTS

WO  WO 2005/096818      10/2005
WO  WO-2005096818  *  10/2005

* cited by examiner

*Primary Examiner*—Alton N Pryor
(74) *Attorney, Agent, or Firm*—Frommer Lawrence & Haug LLP

(57) ABSTRACT

A herbicide composition for paddy field characterized by containing (a) a herbicidal difluoromethanesulfonamide derivative represented by the formula (I)

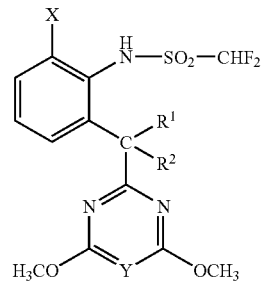

and (b) at least one herbicidal compound selected from the group consisting of pretilachlor, butachlor, alachlor, metolachlor, acetochlor, clomeprop, bromobutide, benfuresate, indanofan, pyrazolate, benzofenap, pyrazoxyfen, pyraclonil, oxaziclomefone, bensulfuron-methyl, azimsulfuron, imazosulfuron, pyrazosulfuron-ethyl, cyclosulfamuron, ethoxysulfuron, halosulfuron-methyl, orthosulfamuron, cinosulfuron, metsulfuron-methyl, penoxsulam, thiobencarb, pyributycarb, molinate, dimethametryn, simetryn, cafenstrole, quinclorac, anilofos, mefenacet, fentrazamide, pentoxazone, oxadiargyl, oxadiazon, benzobicyclon, mesotrione, AVH301 (code no.), cyhalofop-butyl, metamifop, bispyribac-sodium, pyriftalid, pyrimisulfan, pyrimenobac-methyl, chlormethoxynil, oxyfluorfen, dithiopyr, MCPA, MCPB, 2,4-D, dymron, cumyluron, quinoclamine and clomazone, and/or (c) one or more compounds selected from the group consisting of safeners dymron, isoxadifen(-ethyl), flurazole, fenchlorazole-ethyl, fenclorim, cloquintocet-mexyl, oxabetrinil, fluxofenim, mefenpyr-diethyl, furilazole, R-29148 (code no.), benoxacor, dichlormid and dicyclonone as effective components.

13 Claims, No Drawings

HERBICIDE COMPOSITION FOR PADDY FIELD

INCORPORATION BY REFERENCE

This application claims benefit under 35 U.S.C. 119(a) of Japanese patent application 2006-6422, filed on 13 Jan. 2006.

Any foregoing applications, including Japanese patent application 2006-6422, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

The present invention relates to a herbicide composition for a paddy field. More specifically the present invention relates to a herbicide composition for a paddy field containing a herbicidal difluoromethanesulfonamide derivative and a certain kind of known herbicidal compound as effective components.

Difluoromethanesulfonamide (DFMS) derivatives represented by the formula

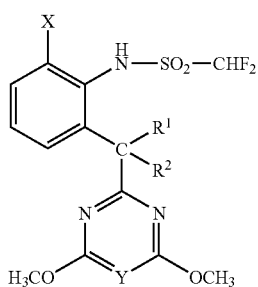

(I)

wherein
X represents a halogen,
Y represents CH or N,
$R^1$ represents hydrogen, and
$R^2$ represents hydrogen or hydroxy, or
$R^1$ and $R^2$ together may form C=O with the carbon atom to which they are bonding, are known compounds (WO-A-2005/096818). Some of these derivatives show good controlling effect against paddy field weeds. However, contrary to expectation, some DFMS compounds do not show a fully satisfactory herbicidal effect and phytotoxicity to paddy rice is observed. In practical usage, it is difficult to provide a single active compound with such properties as to correspond to various kinds of usage, as there are many potential elements influencing the herbicidal effect. Examples of such elements include the kinds of weeds to be controlled, the conditions of their developing area, etc., and as such the effect of an active compound is different. In addition, with regard to considerations of cost reduction in agricultural production, effects on the environment, etc., development of an agent showing effective action with less application amount is also a desired goal.

The invention does not intend to encompass within the scope of the invention any previously disclosed product, process of making the product or method of using the product, which meets the written description and enablement requirements of the USPTO (35 U.S.C. 112, first paragraph) or the EPO (Article 83 of the EPC), such that applicant(s) reserve the right and hereby disclose a disclaimer of any previously described product, method of making the product or process of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are apparent from and encompassed by, the following Detailed Description.

In order to fulfill the desired goal(s), one of the methods to improve properties of a herbicide is to mix it with other active compounds. However, the expected effect of such mixtures is not necessarily obtained due to factors such as decomposition of active compounds, antagonistic action of effects, etc.

The present inventors have found that the composition mentioned below shows an excellent and desirable effect in terms of weed controlling in paddy field and lowering phytotoxicity to rice.

Thus, the present invention provides a herbicide composition for a paddy field comprising a combination of components (a), (b) and/or (c), wherein
(a) is one or more difluoromethanesulfonamide derivative compounds represented by the formula

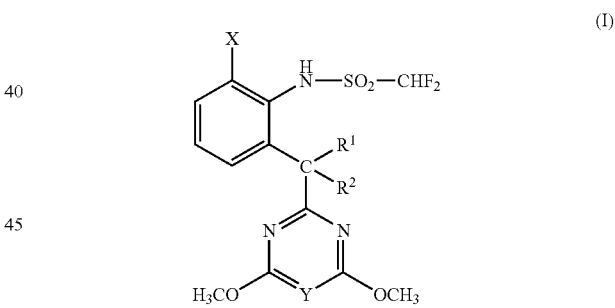

(I)

wherein
X represents a halogen,
Y represents CH or N,
$R^1$ represents hydrogen, and
$R^2$ represents hydrogen or hydroxy, or
$R^1$ and $R^2$ together may form C=O with the carbon atom to which they are bonding,
(b) is one or more herbicidal compounds selected from the group consisting of pretilachlor, butachlor, alachlor, metolachlor, acetochlor, clomeprop, bromobutide, benfuresate, indanofan, pyrazolate, benzofenap, pyrazoxyfen, pyraclonil, oxaziclomefone, bensulfuron-methyl, azimsulfuron, imazosulfuron, pyrazosulfuron-ethyl, cyclosulfamuron, ethoxysulfuron, halosulfuron-methyl, orthosulfamuron, cinosulfuron, metsulfuron-methyl, penoxsulam, thiobencarb, pyributycarb, molinate, dimethametryn, simetryn, cafenstrole, quinclorac, anilofos, mefenacet, fentrazamide, pentoxazone, oxadiargyl, oxadiazon, benzobicyclon, mesotrione, AVH301 (code no.), cyhalofop-butyl, metamifop, bispyribac-sodium, pyriftalid, pyrimisulfan, pyrimenobac-methyl, chlormethoxynil (chlomethoxyfen), oxyfluorfen, dithiopyr, MCPA, MCPB, 2,4-D, dymron, cumyluron, quinoclamine and clomazone, and (c) is one or more safener compounds selected from the group consisting of dymron, isoxadifen(-ethyl), flurazole, fenchlorazole-ethyl, fenclorim, cloquintocet-mexyl, oxabetrinil, fluxofenim, mefenpyr-diethyl, furilazole, R-29148 (code no.), benoxacor, dichlormid and dicyclonone as effective components.

In the following the compounds of components (a), (b) and (c) are also named compounds (a), (b) or (c), respectively. The components (a), (b) and (c) are also shortly named compound (a), (b) or (c) respectively.

Surprisingly, the composition of the present invention, provides a substantially higher herbicidal effect (synergistic effect) than the sum of the effect of each active compound applied individually. As a result, for controlling weeds, it is possible to substantially reduce the concentration of each compound as used previously in the art. At the same time for the composition of the invention, a broad herbicidal spectrum can be obtained and the application period can be increased. In the paddy rice culture, for example, the compositions of the invention show excellent herbicidal effect when applied any time from the early stage of weed development just after the transplantation to growing period. In addition, the effects are maintained for a long period Thus, an excellent herbicidal effect with an excellent residual effect and no phytotoxicity to rice is obtained.

In one embodiment of the invention, the compound (a) of the formula (I) in the composition of the present invention, is defined as a compound of formula (I) wherein:
X represents fluorine or chlorine,
Y represents CH or N,
$R^1$ represents hydrogen, and
$R^2$ represents hydrogen or hydroxy, or
$R^1$ and $R^2$ together may form C=O with the carbon atom to which they are bonding.

In another embodiment of the invention examples of the compound (a) of the formula (I) in the composition of the present invention can be those mentioned in the Table A mentioned below:

TABLE A

| Compound No. | X | Y | $R^1$ | $R^2$ |
|---|---|---|---|---|
| 1 | F | CH | H | OH |
| 2 | F | N | H | OH |
| 3 | Cl | CH | H | OH |
| 4 | Cl | N | H | OH |
| 5 | Br | CH | H | OH |
| 6 | Br | N | H | OH |
| 7 | I | CH | H | OH |
| 8 | I | N | H | OH |
| 9 | F | CH | H | H |
| 10 | F | N | H | H |
| 11 | Cl | CH | H | H |
| 12 | Cl | N | H | H |
| 13 | Br | CH | H | H |
| 14 | Br | N | H | H |
| 15 | I | CH | H | H |
| 16 | I | N | H | H |
| 17 | F | CH | | C=O |
| 18 | F | N | | C=O |
| 19 | Cl | CH | | C=O |
| 20 | Br | CH | | C=O |

TABLE A-continued

| Compound No. | X | Y | $R^1$ | $R^2$ |
|---|---|---|---|---|
| 21 | Br | N | | C=O |
| 22 | I | CH | | C=O |
| 23 | I | N | | C=O |

These compounds can be used individually or in combination of two or more.

In the composition of the present invention, the herbicidal compounds (b) used in combination with the compound (a) of the above-mentioned formula (I) are as aforementioned, and in one embodiment of the invention, examples can be (b-1) anilofos, (b-2) pretilachlor, (b-3) cafenstrole, (b-4) cyhalofop-butyl, (b-5) penoxsulam, (b-6) pyraclonil, (b-7) bispyribac-sodium, (b-8) fentrazamide, (b-9) mefenacet, (b-10) oxaziclomefone, (b-11) benfuresate, (b-12) bensulfuron-methyl, (b-13) ethoxysulfuron, (b-14) bromobutide and (b-15) AVH301.

The above-mentioned herbicidal compounds (b) can be used, individually or in combination of two or more, as a mixture with a compound (a) of the formula (I).

The compounds (c) as safener used in combination with the compound (a) of the above-mentioned formula (I) according to the present invention are as aforementioned, and in one embodiment of the invention examples can be (c-1) dymron, (c-2) mefenpyr-diethyl, (c-3) isoxadifen and (c-4) isoxadifen-ethyl.

The above-mentioned compounds (c) as safener can be used, individually or in combination of two kinds or more, as a mixture with a compound (a) of the formula (I).

The above-mentioned herbicidal compounds (b) and the compounds (c) as safener are described in, for example, The Pesticide Manual, $13^{th}$ edition (published by British Crop Protection Council, 2003) or "Compendium of Pesticide Common Names" (http://www.alanwood.net/pesticides). The compound having the code number AVH 301 is a herbicide having the chemical name 2-{2-chloro-4-mesyl-3-[(tetrahydrofuran-2-ylmethoxy)-methyl]-benzoyl}-cyclohexan-1,3-dione, also known under the common name "tefuryltrione". The compound having the code number R-29148 is a safener having the chemical name 3-(dichloroacetyl)-2,2,5-trimethyl-oxazolidine known from DE-A-02350800 (U.S. Pat. No. 3,989,503).

In the composition of the present invention, the mixing ratio of a compound (a) of the formula (I) and a herbicidal compound (b) can be varied in a relatively wide range according to the kind, application period, application place, application method, etc. of said composition. Generally, at least one herbicidal compounds (b) in the range of 0.05-200 parts by weight, (in another embodiment of the invention, 0.1-100 parts by weight) can be used to 1 part by weight of a compound (a) of the formula (I). Specifically, in one embodiment of the invention for individual usage ratio of herbicidal compounds (b) to 1 part by weight of a compound (a) of the formula (I) there can be mentioned the following embodiments.

Anilofos (b-1): 0.5-50 parts by weight, or 1-20 parts by weight,

Pretilachlor (b-2): 0.5-50 parts by weight, or 1-20 parts by weight,

Cafenstrole (b-3): 0.5-50 parts by weight, or 1-20 parts by weight,

Cyhalofop-butyl (b-4): 0.3-30 parts by weight, or 0.5-10 parts by weight,

Penoxsulam (b-5): 0.2-10 parts by weight, or 1-5 parts by weight,
Pyraclonil (b-6): 0.5-50 parts by weight, or 1-20 parts by weight,
Bispyribac-sodium (b-7): 0.1-10 parts by weight, or 0.2-5 parts by weight,
Fentrazamide (b-8): 0.5-50 parts by weight, or 1-20 parts by weight,
Mefenacet (b-9): 2-200 parts by weight, or 5-50 parts by weight,
Oxaziclomefone (b-10): 0.2-10 parts by weight, or 1-5 parts by weight,
Benfuresate (b-11): 0.5-50 parts by weight, or 1-20 parts by weight,
Bensulfuron-methyl (b-12): 0.1-10 parts by weight, or 0.2-5 parts by weight,
Ethoxysulfuron (b-13): 0.1-10 parts by weight, or 0.2-5 parts by weight,
Bromobutide (b-14): 2-200 parts by weight, or 5-50 parts by weight,
AVH301 (b-15): 0.5-50 parts by weight, or 1-30 parts by weight.

In the composition of the present invention, the mixing ratio of a compound (a) of the formula (I) and a compound (c) as safener can be varied in a relatively wide range according to the kind, application period, application place, application method, etc. of said composition. Generally, at least one compounds (c) as safener in the range of 0.05-200 parts by weight, (in another embodiment of the invention 0.2-100 parts by weight) can be used to 1 part by weight of a compound (a) of the formula (I). Specifically, in one embodiment of the invention for individual usage ratio of compounds (c) to 1 part by weight of a compound (a) of the formula (I) there can be mentioned the following.

Dymron (c-1): 0.5-100 parts by weight, or 1-20 parts by weight,
Mefenpyr-diethyl (c-2): 0.05-10 parts by weight, or 0.5-5 parts by weight,
Isoxadifen (c-3): 0.05-10 parts by weight, or 0.5-5 parts by weight, Isoxadifen-ethyl
(c-4): 0.05-10 parts by weight, or 0.5-5 parts by weight.

The composition of the present invention shows a strong controlling effect against paddy field weeds and therefore said composition can be used as a herbicide composition for paddy field, particularly a selective herbicide for paddy rice.

An object of the invention is thus the use of a combination of herbicide (a) and herbicide (b) or safener (c) or a combination of components (a)+(b)+(c) for controlling weeds in a paddy field, optionally in the presence of a crop of useful plants, particularly rice plants. The components can be applied to the paddy field and its weed plants in sequential manner or simultaneously. Another object of the invention is thus the method wherein the components (a), (b) and/or (c) are applied accordingly.

The composition of the present invention can be used against various kinds of weeds developing in the paddy field. As their examples there can be mentioned the following:

Dicotyledonous plants of the following Genera: *Polygonum, Rorippa, Rotala, Lindernia, Bidens, Dopatrium, Eclipta, Elatine, Gratiola, Lindernia, Ludwigia, Oenanthe, Ranunculus, Deinostema*, etc.

Monocotyledonous plants of the following Genera: *Echinochloa, Panicum, Poa, Cyperus, Monochoria, Fimbristylis, Sagittaria, Eleocharis, Scirpus, Alisma, Aneilema, Blyxa, Eriocaulon, Potamogeton*, etc.

The composition of the present invention can be used, more specifically for example, in relation to the following typical paddy field weeds.

Dicotyledonous Plants
*Rotala indica* Koehne
*Lindernia procumbens* Philcox
*Ludwigia prostrata* Roxburgh
*Potamogeton distinctus* A. Benn
*Elatine triandra* Schk
*Oenanthe javanica*

Monocotyledonous Plants
*Echinochloa oryzicola* Vasing
*Monochoria vaginalis* Presl
*Eleocharis acicularis* L.
*Eleocharis Kuroguwai* Ohwi
*Cyperus difformis* L.
*Cyperus serotinus* Rottboel
*Sagittaria pygmaea* Miq
*Alisma canaliculatum* A. Br. et Bouche
*Scirpus juncoides* Roxburgh The use of the composition of the present invention, however, should not be restricted to these weeds in any way, but can be applied against other weeds in the same manner.

The composition of the present invention can be made into customary formulation forms for control of paddy field weeds. As such formulation forms there can be mentioned, for example, solutions, emulsions, wettable powders, suspensions, powders, soluble powders, granules, suspo-emulsion concentrates, solid formulations (jumbo formulations), floating granules, microcapsules in polymer substance, etc.

These formulations can be prepared according to per se known methods. The formulations according to the present invention can be prepared, for example, by mixing the aforementioned compound (a) of the formula (I), herbicidal compound (b) and/or compound (c) with extenders, namely liquid diluents and/or solid diluents, and, in case of necessity, by using surfactants, namely emulsifiers and/or dispersants and/or foam-forming agents.

In case of using water as extender, for example, organic solvents can be used as auxiliary solvent. As liquid diluents there can be mentioned, for example, organic solvents such as aromatic hydrocarbons (for example, xylene, toluene, alkyl-naphthalene, etc.), chlorinated aromatic or chlorinated aliphatic hydrocarbons (for example, chlorobenzenes, ethylene chlorides, methylene chloride, etc.), aliphatic hydrocarbons (for example, cyclohexane etc. or paraffins (for example, mineral oil fractions, mineral oils, vegetable oils, etc.)), alcohols (for example, butanol, glycols, etc. and their ethers, esters, etc.) ketones (for example, acetone, methyl ethyl ketone, methyl isobutyl ketone, cyclohexanone, etc.), strongly polar solvents (for example, dimethylformamide, dimethyl sulfoxide, etc.), and water.

As solid diluents there can be mentioned, for example, ammonium salts, ground natural minerals (for example, kaolin, clay, talc, chalk, quartz, attapulgite, montmorillonite, diatomaceous earth, etc.), ground synthetic minerals (for example, highly dispersed silicic acid, alumina, silicates, etc.) etc. As solid carriers for powders there can be used, for example, crushed and fractionated rocks (for example, calcite, marble, pumice, sepiolite, dolomite, etc.) synthetic granules of inorganic and organic meals, particles of organic materials (for example, saw dust, coconut shells, maize cobs, tobacco stalks, etc.) etc.

As emulsifiers and/or foaming agents there can be mentioned nonionic or anionic emulsifiers (for example, polyoxyethylene fatty acid esters, polyoxyethylene fatty alcohol ethers (for example, alkylaryl polyglycol ethers, alkylsulfonates, alkylsulfates, arylsulfonates, etc.)), albumin hydrolysis products, etc.

As dispersants, for example, lignin sulfite waste liquor, methyl cellulose, etc. are adequate.

Tackifiers can also be used in formulations (powders, granules, emulsifiable concentrates). As said tackifiers there can be mentioned, for example, carboxymethyl cellulose, natural and synthetic polymers (for example, gum Arabic, polyvinyl alcohol, polyvinyl acetates, etc.) natural phospholipids (for example, cephalins or recithins), synthetic phospholipids, etc. Further, as additives, mineral oils and vegetable oils can be used.

Colorants can also be used. As said colorants there can be mentioned inorganic pigments (for example, iron oxide, titanium oxide, Prussian Blue, etc,), organic dyestuffs such as alizarin dyestuffs, azo dyestuffs or metal phthalocyanine dyestuffs, and further traces nutrients such as salts of iron, manganese, boron, copper, cobalt, molybdenum or zinc.

The formulations can contain the total of the compound of the formula (I) (a), herbicidal compound (b) and/or compound (c) at a concentration in the range of generally 0.1-95% by weight (in another embodiment of the invention 0.5-90% by weight).

The composition of the present invention can be used for controlling weeds as themselves or in their formulation forms. It is also possible to do tank mixing at the time of application and further to contain other known active compounds, particularly active compounds generally used in the paddy field, for example, fungicides, insecticides, plant growth regulators, plant nutrients, soil improving agents, etc.

The composition of the present invention can be used as such or in their formulation forms or in application forms prepared by further diluting said formulations, for example, in the forms of ready-to-use solutions, emulsifiable concentrates, suspensions, powders, wettable powders or granules. Formulations of these forms can be applied to paddy field by usual methods, for example, watering, spraying, atomizing, dusting, granule spreading, etc.

The composition of the present invention can be applied to the paddy field before, at the time and after the transplantation. The amount of said composition to be applied can be varied in a substantial range. The amount can be in the range of, for example, 0.01-5 kg/ha (in another embodiment of the invention 0.06-4.5 kg/ha) as the total amount of the compound of the formula (I) (a), herbicidal compound (b) and/or compound (c).

The invention is further described by the following non-limiting examples which further illustrate the invention, and are not intended, nor should they be interpreted to, limit the scope of the invention.

BIOLOGICAL TEST EXAMPLES AND FORMULATION EXAMPLES

Test Compounds

Component (a) (a-1): compound No. 1 (ref: the aforementioned Table A)
(a-2): compound No. 3 (same as above)
(a-3): compound No. 11 (same as above)
Component (b) the aforementioned (b-1)-(b-15)
Component (c) the aforementioned (c-1)-(c-3)

<Preparation of Test Agents>
Carrier: Acetone 5 parts by weight
Surfactant: Benzyloxy polyglycol ether 1 part by weight The above-mentioned carrier and surfactant and 1 part by weight of active compounds (component (a) and component (b) or component (c)) are mixed and the obtained formulations are diluted with water to prepare the test agents of the prescribed chemicals amount (preparations).

Test Example 1

Test of Effect of the Herbicide Composition Against Paddy Field Weeds

<Test Method>

In a green house, seeds or tubers of *Monochoria vaginalis* Presl, annual broad-leaves (*Lindernia procumbens* Philcox, *Rotala indica* Koehne, *Elatine triandra* Schk, *Ammannia multiflora* Roxb., etc.), *Cyperus serotinus* Rottboel, and *Sagittaria pygmaea* Miq were inoculated to paddy field soil filled in a 500 cm$^2$ pot and brought to a submerged condition of about 2-3 cm. At 1.5-2 leafstage of each weed prescribed diluted solution of preparation of each active compound and each herbicide in the following table was applied on water surface each singly or simultaneously. After the treatment, the submerged condition of 3 cm was maintained and the herbicidal effect was studied 3 weeks after the treatment. The herbicidal effect was evaluated as 100% in case of complete death and 0% in case of no effect.

<Results>

Results are shown in Table 1-Table 3. In the tables, MOOVP represents *Monochoria vaginalis* Presl, BBBBB represents annual broad-leaves, CYPSE represents *Cyperus serotinus* Rottboel and SAGPY represents *Sagittaria pygmaea* Miq.

TABLE 1

| Active component | Amount of effective component g/ha | Herbicidal effect (%) | | | |
|---|---|---|---|---|---|
| | | MOOVP | BBBBB | CYPSE | SAGPY |
| (a-1) | 2.5 | 40 | 70 | 80 | 60 |
| +(b-1) | +200 | 90 | 100 | 90 | 70 |
| | +100 | 70 | 80 | 80 | 70 |
| Single | 200 | 10 | 0 | 0 | 10 |
| | 100 | 10 | 0 | 0 | 10 |
| +(b-2) | +250 | 100 | 100 | 80 | 90 |
| | +125 | 70 | 90 | 80 | 80 |
| Single | 250 | 20 | 10 | 0 | 10 |
| | 125 | 10 | 10 | 0 | 0 |
| +(b-3) | +150 | 100 | 100 | 100 | 90 |
| | +75 | 90 | 100 | 80 | 70 |
| Single | 150 | 60 | 50 | 70 | 10 |
| | 75 | 50 | 40 | 0 | 10 |
| +(b-4) | +180 | 50 | 70 | 80 | 70 |
| | +90 | 40 | 70 | 70 | 60 |
| Single | 180 | 10 | 0 | 0 | 20 |
| | 90 | 0 | 0 | 0 | 10 |
| +(b-5) | +100 | 90 | 90 | 100 | 80 |
| | +50 | 80 | 90 | 100 | 80 |
| Single | 100 | 90 | 90 | 70 | 85 |
| | 50 | 75 | 50 | 70 | 65 |
| +(b-6) | +100 | 90 | 100 | 100 | 90 |
| | +50 | 90 | 100 | 100 | 80 |
| Single | 100 | 90 | 90 | 30 | 85 |
| | 50 | 80 | 90 | 20 | 50 |
| +(b-7) | +5 | 70 | 90 | 100 | 80 |
| | +2.5 | 40 | 80 | 90 | 80 |
| Single | 5 | 10 | 10 | 60 | 30 |
| | 2.5 | 0 | 10 | 20 | 0 |
| +(b-8) | +150 | 100 | 100 | 100 | 90 |
| | +75 | 90 | 85 | 100 | 80 |

TABLE 1-continued

| Active component (a-1) | Amount of effective component g/ha 2.5 | Herbicidal effect (%) | | | |
|---|---|---|---|---|---|
| | | MOOVP 40 | BBBBB 70 | CYPSE 80 | SAGPY 60 |
| Single | 150 | 60 | 70 | 30 | 30 |
| | 75 | 40 | 40 | 30 | 30 |
| +(b-9) | +600 | 100 | 90 | 100 | 80 |
| | +300 | 100 | 90 | 80 | 70 |
| Single | 600 | 80 | 40 | 30 | 10 |
| | 300 | 65 | 30 | 30 | 10 |
| +(b-10) | +40 | 80 | 90 | 100 | 80 |
| | +20 | 60 | 70 | 70 | 60 |
| Single | 40 | 20 | 40 | 0 | 10 |
| | 20 | 10 | 40 | 0 | 0 |
| +(b-11) | +250 | 70 | 90 | 100 | 80 |
| | +125 | 60 | 80 | 100 | 50 |
| Single | 250 | 0 | 0 | 70 | 20 |
| | 125 | 0 | 0 | 20 | 10 |
| +(b-12) | +5 | 70 | 100 | 100 | 95 |
| | +2.5 | 50 | 90 | 100 | 80 |
| Single | 5 | 60 | 60 | 40 | 50 |
| | 2.5 | 30 | 50 | 40 | 50 |
| +(b-13) | +3 | 85 | 100 | 100 | 90 |
| | +1.5 | 80 | 85 | 90 | 75 |
| Single | 3 | 70 | 70 | 0 | 65 |
| | 1.5 | 65 | 40 | 0 | 65 |
| +(b-14) | +400 | 90 | 80 | 90 | 70 |
| | +200 | 70 | 50 | 85 | 70 |
| Single | 400 | 95 | 30 | 60 | 10 |
| | 200 | 30 | 20 | 40 | 10 |
| +(b-15) | +150 | 100 | 90 | 90 | 80 |
| | +75 | 100 | 80 | 80 | 80 |
| Single | 150 | 95 | 65 | 85 | 80 |
| | 75 | 85 | 50 | 80 | 80 |

TABLE 2

| Active component (a-2) | Amount of effective component g/ha 2.5 | Herbicidal effect (%) | | | |
|---|---|---|---|---|---|
| | | MOOVP 30 | BBBBB 60 | CYPSE 75 | SAGPY 60 |
| +(b-1) | +200 | 90 | 100 | 90 | 70 |
| | +100 | 60 | 70 | 70 | 60 |
| Single | 200 | 10 | 0 | 0 | 10 |
| | 100 | 10 | 0 | 0 | 10 |
| +(b-2) | +250 | 95 | 95 | 70 | 90 |
| | +125 | 80 | 85 | 40 | 70 |
| Single | 250 | 20 | 10 | 0 | 10 |
| | 125 | 10 | 10 | 0 | 0 |
| +(b-3) | +150 | 100 | 100 | 100 | 85 |
| | +75 | 90 | 90 | 70 | 80 |
| Single | 150 | 60 | 50 | 70 | 10 |
| | 75 | 50 | 40 | 0 | 10 |
| +(b-4) | +180 | 60 | 70 | 95 | 80 |
| | +90 | 50 | 70 | 70 | 80 |
| Single | 180 | 10 | 0 | 0 | 20 |
| | 90 | 0 | 0 | 0 | 10 |
| +(b-5) | +100 | 85 | 95 | 100 | 80 |
| | +50 | 85 | 90 | 95 | 70 |
| Single | 100 | 90 | 90 | 70 | 85 |
| | 50 | 75 | 50 | 70 | 65 |
| +(b-6) | +100 | 95 | 100 | 100 | 85 |
| | +50 | 90 | 100 | 70 | 80 |
| Single | 100 | 90 | 90 | 30 | 85 |
| | 50 | 80 | 90 | 20 | 50 |
| +(b-7) | +5 | 60 | 85 | 100 | 80 |
| | +2.5 | 40 | 60 | 90 | 80 |
| Single | 5 | 10 | 10 | 60 | 30 |
| | 2.5 | 0 | 10 | 20 | 0 |
| +(b-8) | +150 | 100 | 100 | 100 | 85 |
| | +75 | 90 | 85 | 95 | 85 |

TABLE 2-continued

| Active component (a-2) | Amount of effective component g/ha 2.5 | Herbicidal effect (%) | | | |
|---|---|---|---|---|---|
| | | MOOVP 30 | BBBBB 60 | CYPSE 75 | SAGPY 60 |
| Single | 150 | 60 | 70 | 30 | 30 |
| | 75 | 40 | 40 | 30 | 30 |
| +(b-9) | +600 | 100 | 90 | 100 | 70 |
| | +300 | 90 | 85 | 70 | 70 |
| Single | 600 | 80 | 40 | 30 | 10 |
| | 300 | 65 | 30 | 30 | 10 |
| +(b-10) | +40 | 70 | 80 | 95 | 80 |
| | +20 | 40 | 60 | 70 | 70 |
| Single | 40 | 20 | 40 | 0 | 10 |
| | 20 | 10 | 40 | 0 | 0 |
| +(b-11) | +250 | 80 | 90 | 100 | 70 |
| | +125 | 50 | 60 | 80 | 50 |
| Single | 250 | 0 | 0 | 70 | 20 |
| | 125 | 0 | 0 | 20 | 10 |
| +(b-12) | +5 | 85 | 90 | 100 | 70 |
| | +2.5 | 50 | 80 | 100 | 70 |
| Single | 5 | 60 | 60 | 40 | 50 |
| | 2.5 | 30 | 50 | 40 | 50 |
| +(b-13) | +3 | 85 | 80 | 100 | 80 |
| | +1.5 | 80 | 80 | 80 | 75 |
| Single | 3 | 70 | 70 | 0 | 65 |
| | 1.5 | 65 | 40 | 0 | 65 |
| +(b-14) | +400 | 90 | 70 | 90 | 80 |
| | +200 | 40 | 50 | 90 | 60 |
| Single | 400 | 95 | 30 | 60 | 10 |
| | 200 | 30 | 20 | 40 | 10 |
| +(b-15) | +150 | 90 | 85 | 90 | 80 |
| | +75 | 100 | 70 | 80 | 85 |
| Single | 150 | 95 | 65 | 85 | 80 |
| | 75 | 85 | 50 | 80 | 80 |

TABLE 3

| Active component (a-3) | Amount of effective component g/ha 5.0 | Herbicidal effect (%) | | | |
|---|---|---|---|---|---|
| | | MOOVP 30 | BBBBB 60 | CYPSE 50 | SAGPY 50 |
| +(b-1) | +200 | 70 | 80 | 90 | 70 |
| | +100 | 50 | 50 | 70 | 60 |
| Single | 200 | 10 | 0 | 0 | 10 |
| | 100 | 10 | 0 | 0 | 10 |
| +(b-2) | +250 | 70 | 80 | 60 | 70 |
| | +125 | 50 | 75 | 40 | 60 |
| Single | 250 | 20 | 10 | 0 | 10 |
| | 125 | 10 | 10 | 0 | 0 |
| +(b-3) | +150 | 90 | 90 | 100 | 70 |
| | +75 | 90 | 85 | 60 | 60 |
| Single | 150 | 60 | 50 | 70 | 10 |
| | 75 | 50 | 40 | 0 | 10 |
| +(b-4) | +180 | 50 | 60 | 80 | 70 |
| | +90 | 30 | 60 | 60 | 70 |
| Single | 180 | 10 | 0 | 0 | 20 |
| | 90 | 0 | 0 | 0 | 10 |
| +(b-5) | +100 | 80 | 95 | 90 | 90 |
| | +50 | 85 | 90 | 80 | 70 |
| Single | 100 | 90 | 90 | 70 | 85 |
| | 50 | 75 | 50 | 70 | 65 |
| +(b-6) | +100 | 100 | 100 | 80 | 100 |
| | +50 | 90 | 100 | 70 | 80 |
| Single | 100 | 90 | 90 | 30 | 85 |
| | 50 | 80 | 90 | 20 | 50 |
| +(b-7) | +5 | 50 | 80 | 100 | 80 |
| | +2.5 | 30 | 75 | 80 | 70 |
| Single | 5 | 10 | 10 | 60 | 30 |
| | 2.5 | 0 | 10 | 20 | 0 |
| +(b-8) | +150 | 90 | 90 | 80 | 80 |
| | +75 | 60 | 85 | 80 | 80 |

TABLE 3-continued

| Active component (a-3) | Amount of effective component g/ha 5.0 | Herbicidal effect (%) | | | |
|---|---|---|---|---|---|
| | | MOOVP 30 | BBBBB 60 | CYPSE 50 | SAGPY 50 |
| Single | 150 | 60 | 70 | 30 | 30 |
|  | 75 | 40 | 40 | 30 | 30 |
| +(b-9) | +600 | 90 | 90 | 90 | 70 |
|  | +300 | 80 | 85 | 80 | 60 |
| Single | 600 | 80 | 40 | 30 | 10 |
|  | 300 | 65 | 30 | 30 | 10 |
| +(b-10) | +40 | 70 | 80 | 80 | 70 |
|  | +20 | 50 | 70 | 70 | 70 |
| Single | 40 | 20 | 40 | 0 | 10 |
|  | 20 | 10 | 40 | 0 | 0 |
| +(b-11) | +250 | 50 | 60 | 90 | 70 |
|  | +125 | 40 | 60 | 70 | 70 |
| Single | 250 | 0 | 0 | 70 | 20 |
|  | 125 | 0 | 0 | 20 | 10 |
| +(b-12) | +5 | 80 | 95 | 90 | 85 |
|  | +2.5 | 40 | 90 | 90 | 70 |
| Single | 5 | 60 | 60 | 40 | 50 |
|  | 2.5 | 30 | 50 | 40 | 50 |
| +(b-13) | +3 | 80 | 90 | 70 | 80 |
|  | +1.5 | 80 | 90 | 50 | 80 |
| Single | 3 | 70 | 70 | 0 | 65 |
|  | +1.5 | 65 | 40 | 0 | 65 |
| +(b-14) | +400 | 90 | 80 | 90 | 80 |
|  | +200 | 60 | 60 | 70 | 70 |
| Single | 400 | 95 | 30 | 60 | 10 |
|  | 200 | 30 | 20 | 40 | 10 |
| +(b-15) | +150 | 90 | 100 | 90 | 90 |
|  | +75 | 90 | 80 | 70 | 85 |
| Single | 150 | 95 | 65 | 85 | 80 |
|  | 75 | 85 | 50 | 80 | 80 |

Test Example 2

Test of Effect of Phytotoxicity Reduction

<Test Method>

In a green house, paddy rice of 2-2.5 leafstage was transplanted to paddy field soil filled in a 1000 cm² pot to 2 cm depth and brought to a submerged condition of about 2-3 cm. Five days after the transplantation, prescribed diluted solution of preparation of each active compound and each herbicide in the following table was applied on water surface each singly or simultaneously. After the treatment, the submerged condition of 3 cm was maintained and the grade of phytotoxicity to paddy rice was studied 2 weeks after the treatment. The phytotoxicity was evaluated as 100% in case of complete death and 0% in case of no phytotoxicity.

<Results>

Results are shown in Table 4.

TABLE 4

| Active component | Amount of effective component (g/ha) | Phytotoxicity % |
|---|---|---|
| (a-1) | 120 | 50 |
|  | 60 | 30 |
| +(c-1) | 120 + 450 | 30 |
|  | 60 + 450 | 20 |
| +(c-2) | 120 + 500 | 30 |
|  | 60 + 500 | 20 |
| +(c-3) | 120 + 500 | 45 |
|  | 60 + 500 | 20 |

TABLE 4-continued

| Active component | Amount of effective component (g/ha) | Phytotoxicity % |
|---|---|---|
| (a-2) | 120 | 40 |
|  | 60 | 20 |
| +(c-1) | 120 + 450 | 25 |
|  | 60 + 450 | 10 |
| +(c-2) | 120 + 500 | 25 |
|  | 60 + 500 | 10 |
| +(c-3) | 120 + 500 | 35 |
|  | 60 + 500 | 10 |
| (a-3) | 180 | 30 |
|  | 90 | 20 |
| +(c-1) | 180 + 450 | 10 |
|  | 90 + 450 | 0 |
| +(c-2) | 180 + 500 | 20 |
|  | 90 + 500 | 10 |
| +(c-3) | 180 + 500 | 25 |
|  | 90 + 500 | 10 |
| (c-1) | 450 | 0 |
| (c-2) | 500 | 0 |
| (c-3) | 500 | 0 |

Formulation Example 1

To a mixture of 3 parts by weight of the active compound (a-1), 4 parts by weight of the active compound (b-1), 32 parts by weight of bentonite (montmorillonite), 58 parts by weight of talc and 3 parts by weight of ligninsulfonate salt, 25 parts by weight of water were added, well kneaded, made into granules of 10-40 mesh by an extrusion granulator and dried at 40-50° C. to obtain granules.

Formulation Example 2

96 Parts by weight of clay mineral particles having particle diameter distribution in the range of 0.2-2 mm are put in a rotary mixer. While rotating it, 2 parts by weight of the active compound (a-1) and 2 parts by weight of the active compound (b-2) are sprayed together with a liquid diluent, wetted uniformly and dried at 40-50° C. to obtain granules.

Formulation Example 3

A mixture of 4 parts by weight of the active compound (a-1), 4 parts by weight of the active compound (b-3), 10 parts by weight of ethylene glycol, 3 parts by weight of polyoxyalkylene tristyrylphenyl ether, 10 parts by weight of xanthan gum, 0.5 parts by weight of 14% silicone oil emulsion and 68.5 parts by weight of water is well stirred and then crushed with a crusher (Dyno-Mill Type KDL) to obtain water suspension formulation.

Formulation Example 4

5 Parts by weight of the active compound (a-1), 15 parts by weight of the active compound (b-4), 30 parts by weight of sodium ligninsulfonate, 15 parts by weight of parts bentonite and 35 parts by weight of calcined diatomaceous earth powder are well mixed, added with water, well kneaded, extruded with 0.3 mm screen and dried to obtain water dispersible granules.

INDUSTRIAL APPLICABILITY

The herbicide composition for paddy field of the present invention shows, as shown in the aforementioned test examples, precise controlling effect against various kinds of paddy field weeds and an excellent residual effect.

Having thus described in detail various embodiments of the present invention, it is to be understood that the invention defined by the above paragraphs is not to be limited to particular details set forth in the above description as many apparent variations thereof are possible without departing from the spirit or scope of the present invention.

The invention claimed is:

1. A herbicide composition for a paddy field characterized by comprising a synergistic combination of components (a) and (b), wherein
   (a) is one or more difluoromethanesulfonamide derivatives represented by the formula (I),

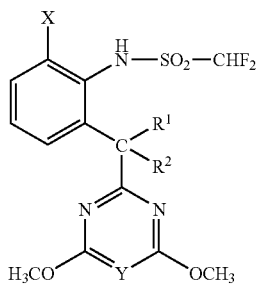

(I)

wherein
X represents fluorine,
Y represents CH or N,
$R^1$ represents hydrogen, and
$R^2$ represents hydroxy,
and (b) is ethoxysulfuron.

2. A composition according to claim 1, characterized in that
Y represents N.

3. A composition according to claim 1, characterized in that
Y represents CH.

4. A composition according to claim 1, characterized in that it comprises compound (b) in the range of 0.05-200 parts by weight to 1 part by weight of the compound (a).

5. A composition as claimed in claim 2, characterized in that it comprises compound (b) in the range of 0.05-200 parts by weight to 1 part by weight of the compound (a).

6. A composition as claimed in claim 3, characterized in that it comprises compound (b) in the range of 0.05-200 parts by weight to 1 part by weight of the compound (a).

7. Method for controlling weeds in a paddy field which comprises applying to the weeds, parts of the weeds, weed seeds or their habitat, optionally in the presence of a crop, the herbicidal composition of claim 1
wherein the components (a) and (b) are applied simultaneously or sequentially, and wherein the components are defined as in claim 1.

8. Method as claimed in claim 7, characterized in that
Y represents or N.

9. Method as claimed in claim 7, characterized in that
Y represents CH.

10. Method as claimed in claim 7, wherein the crop is rice.

11. Method according to claim 7, characterized in that it comprises compound (b) in the range of 0.05-200 parts by weight to 1 part by weight of the compound (a).

12. Method according to claim 8, characterized in that it comprises compound (b) in the range of 0.05-200 parts by weight to 1 part by weight of the compound (a).

13. Method according to claim 9, characterized in that it comprises compound (b) in the range of 0.05-200 parts by weight to 1 part by weight of the compound (a).

* * * * *